United States Patent [19]

Shen

[11] 4,317,363
[45] Mar. 2, 1982

[54] ELASTOMER INSTRUMENT

[75] Inventor: Linus L. Shen, Libertyville, Ill.

[73] Assignee: Abbott Laboratories, North Chicago, Ill.

[21] Appl. No.: 160,060

[22] Filed: Jun. 16, 1980

[51] Int. Cl.³ .............................................. G01N 33/48
[52] U.S. Cl. ...................................................... 73/64.1
[58] Field of Search ................................... 73/64.1, 59

[56] References Cited

U.S. PATENT DOCUMENTS

| | | | |
|---|---|---|---|
| 3,714,815 | 2/1973 | Hartert | 73/64.1 |
| 4,045,999 | 9/1977 | Palmer | 73/59 |
| 4,148,216 | 4/1979 | Do et al. | 73/64.1 X |
| 4,193,293 | 3/1980 | Cavallari | 73/64.1 |
| 4,202,204 | 5/1980 | Hartert | 73/64.1 |

FOREIGN PATENT DOCUMENTS

| | | | |
|---|---|---|---|
| 1096083 | 11/1959 | Fed. Rep. of Germany | 73/64.1 |
| 1558516 | 1/1969 | France | 73/64.1 |
| 43-12518 | 6/1968 | Japan | 73/59 |
| 507805 | 4/1976 | U.S.S.R. | 73/64.1 |
| 602825 | 4/1978 | U.S.S.R. | 73/64.1 |

OTHER PUBLICATIONS

Hermans, J. Jr., *Investigation of Elastic Properties of Hydrocolloids,* Journal of Poly. Sci., Part A, vol. 3, pp. 1859–1868, 1965.

Carr, N. E. et al., *A Physical Standard of Fibrinogen,* In Anal. Bio. 72, pp. 202–211, 1976.

Shen, L. L. et al., *Differential Activities of Heparins in Plasma,* Thrombosis Research, 13, pp. 671–679, 1978.

*Primary Examiner*—Kyle L. Howell
*Assistant Examiner*—Joseph W. Roskos
*Attorney, Agent, or Firm*—Gildo E. Fato; Robert L. Niblack

[57]   ABSTRACT

An elastometer for measuring the mechanical strength of biological gels such as blood or fibrin clots. Thus this device may be used for accessing anticoagulant and fibrinolitic activities, particularly with respect to drug evaluation. The instrument can also be used to study abnormalities in the blood clotting process, i.e. for clinical diagnosis purposes. The elastometer instrument consists primarily of four basic components: (1) a main body frame including a sample cup holder having a channel therein for circulating fluid to maintain constant temperature of the testing sample; (2) a sample disk and transducer core assembly concentrically suspended in the sample cup by a thin steel wire from an accurate positioning device or micro-manipulator; whereby clots are formed in the gap between the sample cup and the sample disc; (3) an electromagnetic device for applying variable amounts of shear stress via the sample disk to the sample; and (4) a transducer assembly for measuring displacement of the sample subject to a specified shear stress. The instrument includes specially designed clamps for supporting the wire from which the sample disk and transducer core assembly are suspended and precisely adjustable slide assemblies for critical positioning and control of the transducer and electromagnets.

8 Claims, 10 Drawing Figures

ELASTOMER INSTRUMENT

BACKGROUND OF THE INVENTION

The conventional techniques in blood coagulation research are primarily based on the determination of clotting or lysis times, procedures which record the moment when phase transitions take place. These techniques tend to treat clotting time as the end point of a coagulation process, and lysis time as the only major event occurring during fibrinolysis. These conventional techniques consequently confine the research domain within narrow limits. In view of this difficulty, a technique identified as rigidity measurement or elasticity measurement has gained increasing importance in the study of various problems in blood coagulation. This technique provides a unique method with which to follow the entire clotting and gelation processes and thus adds new dimensions to the study of blood coagulation problems. The technique is superior since the parameter (rigidity modulus, G) being measured best reflects the physiological function or pathological effect of the fibrin (plasma or blood) clots.

Different devices have been used for the measurement of clot rigidity. They include the simple device for measuring the tensile strength of fibrin strips (Ware et al. Archives Biochemistry, 13, 231, 1947), a photoelastic wave propagation method (Ferry and Morrison, J. Amer. Chem. Soc., 69, 388, 1947), the thrombelastograph method (Hartert, Ztschr, Ges. Exper. Med., 117, 189, 1951), the use of a viscoelastorecorder (Kaibara and Fukada, Biorheology, 6,329, 1970), the sophisticated Weissenberg rheogoniometer for measuring the complex dynamic viscoelasticity of the gel (Copley et al. Biorheology, 7,81, 1970, Glover et al. Thrombosis Res, 7,185, 1975, Overholser et al. Biorheology, 12,309, 1975), and the use of a Couette elastometer for measuring the static elasticity of fibrin gels as described by Hermans et al, J. in Polymer Sciences, 3, 1859, (1965) and Shen et al, Biochemical Biophysical Res. Communications, 56, 793, (1974), Federation Proceedings, 34,345, (1975), Thrombosis Res, 6,255, (1975).

The invention will be better understood with reference to the following description.

DRAWINGS

SUMMARY OF THE INVENTION

An elastometer for measuring the mechanical strength of biological gels such as blood or fibrin clots. Thus this device may be used for accessing anticoagulant and fibrinolitic activities, particularly with respect to drug evaluation. The instrument can also be used to study abnormalities in the blood clotting process, i.e. for clinical diagnosis purposes. The elastometer instrument consists primarily of four basic components: (1) a main body frame including a sample cup holder having a channel therein for circulating fluid to maintain constant temperature of the testing sample, (2) a sample disk and transducer core assembly concentrically suspended in the sample cup by a thin steel wire from an accurate positioning device or micro-manipulator, the disk applying shear stress to the sample, (3) an electromagnetic device for applying variable amounts of shear stress via the sample disk to the sample, and (4) a transducer assembly for measuring displacement of the sample subject to a specified shear stress. The instrument includes specially designed clamps for supporting the wire from which the sample disk and transducer core assembly are suspended and precisely adjustable slide assemblies for critical positioning and control of the transducer and electromagnets.

The precise adjustment features of the present invention, namely the micromanipulator for positioning the disk precisely and the slide assemblies for precise positioning and control of the transducer and electromagnets, permit accurate and reproducible results. In many prior instruments, these functions were fixed and hence not adjustable. Likewise, with many prior instruments, only qualitative results could be obtained.

DETAILED DESCRIPTION

Figure 2:
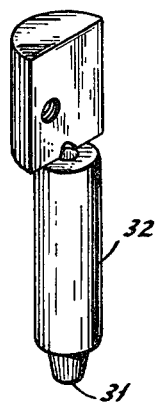
FIG. 2 is a perspective view of the upper wire clamp.
Figure 3:
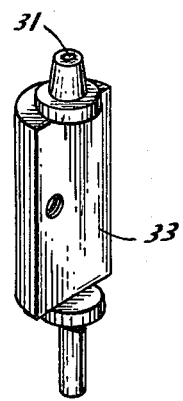
FIG. 3 is a perspective view of the lower wire clamp.
Figure 1:
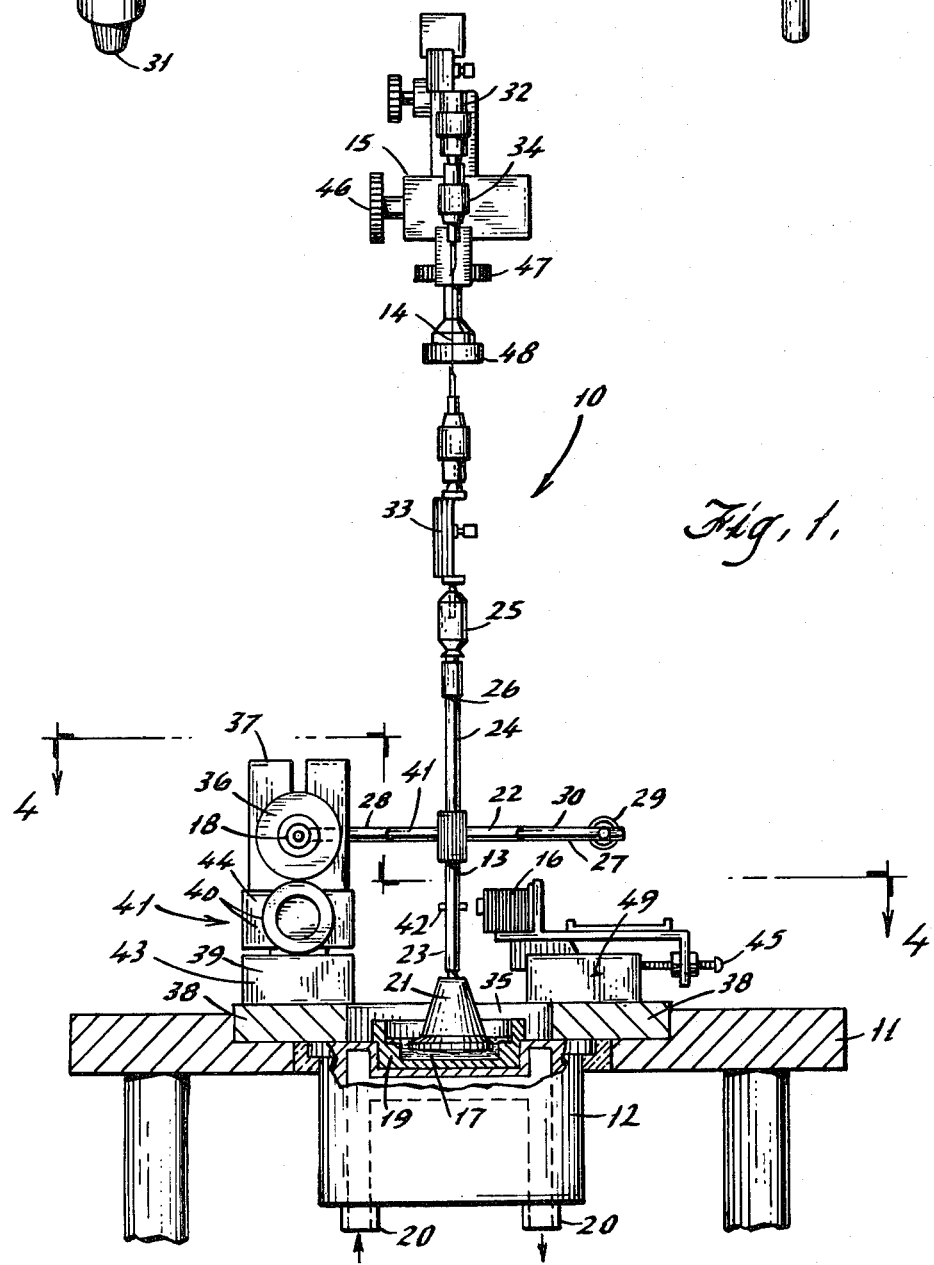
FIG. 1 is a side elevational view illustrating an instrument of the present invention.
Figure 4:
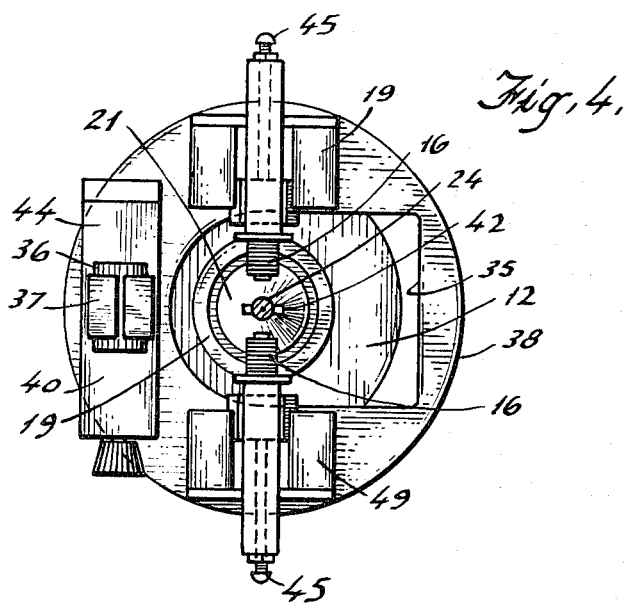
FIG. 4 is a top plan view of the mounting plate, slide assembly and sample cup portion of the instrument as viewed along the line 4—4 in FIG. 1.
Figure 5:
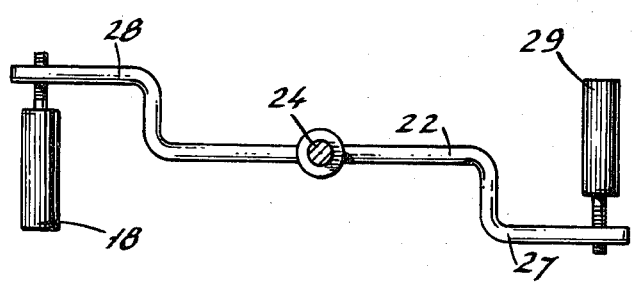
FIG. 5 is a top plan view of the transducer core assembly portion of the instrument.
Figure 6:
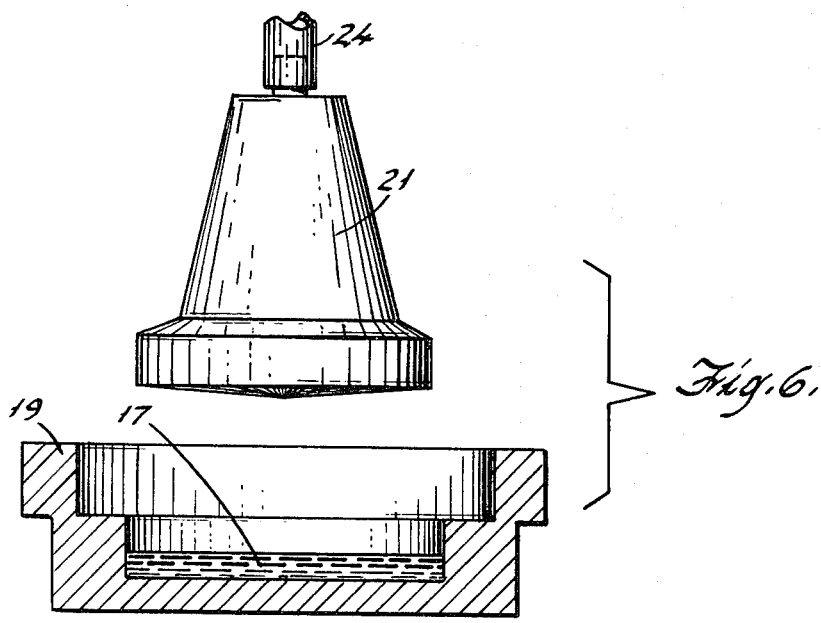
FIG. 6 is a side elevational view illustrating the sample cup and disk assembly.

FIG. 1 illustrates the elastometer 10 and its main components. The instrument consists primarily of four basic parts: (1) the main body frame 11 with water-circulated sample cup holder 12, (2) the sample disk 21 and transducer core assembly 22 suspended by a thin steel wire 14 from a positioning device 15, (3) the electromagnetic device 16 for applying variable amounts of shear stress to the gel 17, and (4) the transducer 18 and the amplifier-indicator unit for measuring displacement of the gel 17 subject to certain shear stress. A conventional amplifier-indicator unit is utilized. The stainless steel sample cup 19 may be secured in the center of the holder 12 in the instrument frame 11 and water circulated through the channels 20 in the cup holder 12 to maintain constant temperature. The sample disk and transducer core assembly 22 consists of a bell-shaped, exchangeable stainless steel disk 21 which is attached to the lower end 23 of a vertical connecting rod 24 with a mounting chuck 25 at the other end 26. A horizontal transducer core arm 27 (FIG. 5) is secured approximately to the middle of the vertical rod 24, the transducer core 18 is attached to one end 28 of the arm and a counterbalance 29 to the other end 30. The arm 27 is symmetrical, assuring good balance. The disk 21 and transducer core 22 assembly is suspended from a micromanipulator 15 (Narishige type MM-2 miniature micromanipulator) by a short segment of steel suture wire 14 (Ethi-Pack surgical steel, size 6-0). A pair of specially designed wire clamps 32, 33 (see FIGS. 2 and 3 for details) are used to facilitate the connection of the steel wire 31 to the mounting chuck 25 at the lower end and to the micromanipulator 15 at the upper end. A syringe needle hub 34 is used with each wire clamp 32, 33 for centering of the steel wire 31 to the middle of the opening 31 of the wire clamps 32, 33. The micromanipulator 15 provides fine adjustments of the position of the sample disk 21 in all three directions. An AC-operated linear variable differential transducer 36 (LVDT) such as Schaevitz model 050 HR, Pennsanken, N.H.), is fastened in an aluminum mounting block 37 which is in turn mounted to the circular rotational mounting plate 38 with the use of two slide assemblies 41 (Velmex, Inc., E. Bloomfield, N.Y.) at a distance equal to the length of the core-arm 27. The two slide assemblies 39, 40 provide "in" and "out" positions of the LVDT 36 for the position during measurement and the position before and after measurement when the LVDT 36 should be kept away from any obstruction during sample preparation. Slide assembly 40 provides fine adjustment for the LVDT 36 along the tangential direction to the rotational mounting plate 38. The linear displacement of the LVDT core 18 in the LVDT 36 body may be read by a transducer-amplifier indicator (such as the Daytronic Model 300D, with type 72 two-channel differential transformer input unit). Torque is applied to the inner disk 21 electromagnetically using two magnetic coils 16 which are oriented 90° to a magnetic bar 42 embedded in the center rod 24 above the disk 21. The two magnetic coils 16 (obtained from Potter and Brumfield type 259 relays) are mounted 180° face-to-face to the center of the rotational mounting plate 38 with the use of the two half-split slide assemblies 49 which also provide "in" and "out" positions for the magnetic coils 16. The exact position of the coils 16 during measurement (the "in" position) may be pre-set by adjustment screws 45 to an ideal stopping position which will result in maximum magnetic torque to the inner disk 21. A Heathkit Model IP-18 regulated DC power supply, used with a Simpson Model 250 VOM, is suitable providing adequate DC current to the electromagnetic device.

The configuration or relative distance between each component described is important and should be pre-set before using the instrument 10.

Each component should be aligned either perpendicular or parallel to the other. Location of each component should always be either symmetrical or tangential to the center or center line of the instrument 10 and the entire instrument 10 should be leveled before pre-setting.

Different designs of sample cup 19 and disk 21 can be used for different purposes. For the measurement of weaker gels, a large cup 19, disk 21 combination (40 mm diameter, 10 ml sample capacity) may be used to maintain greater stability. For gels with rigidity modulus larger than 100 dynes/cm$^2$, a small cup 19, disk 21 combination (29 mm diameter, 2 ml sample capacity) is suitable for measurements.

Figure 9:
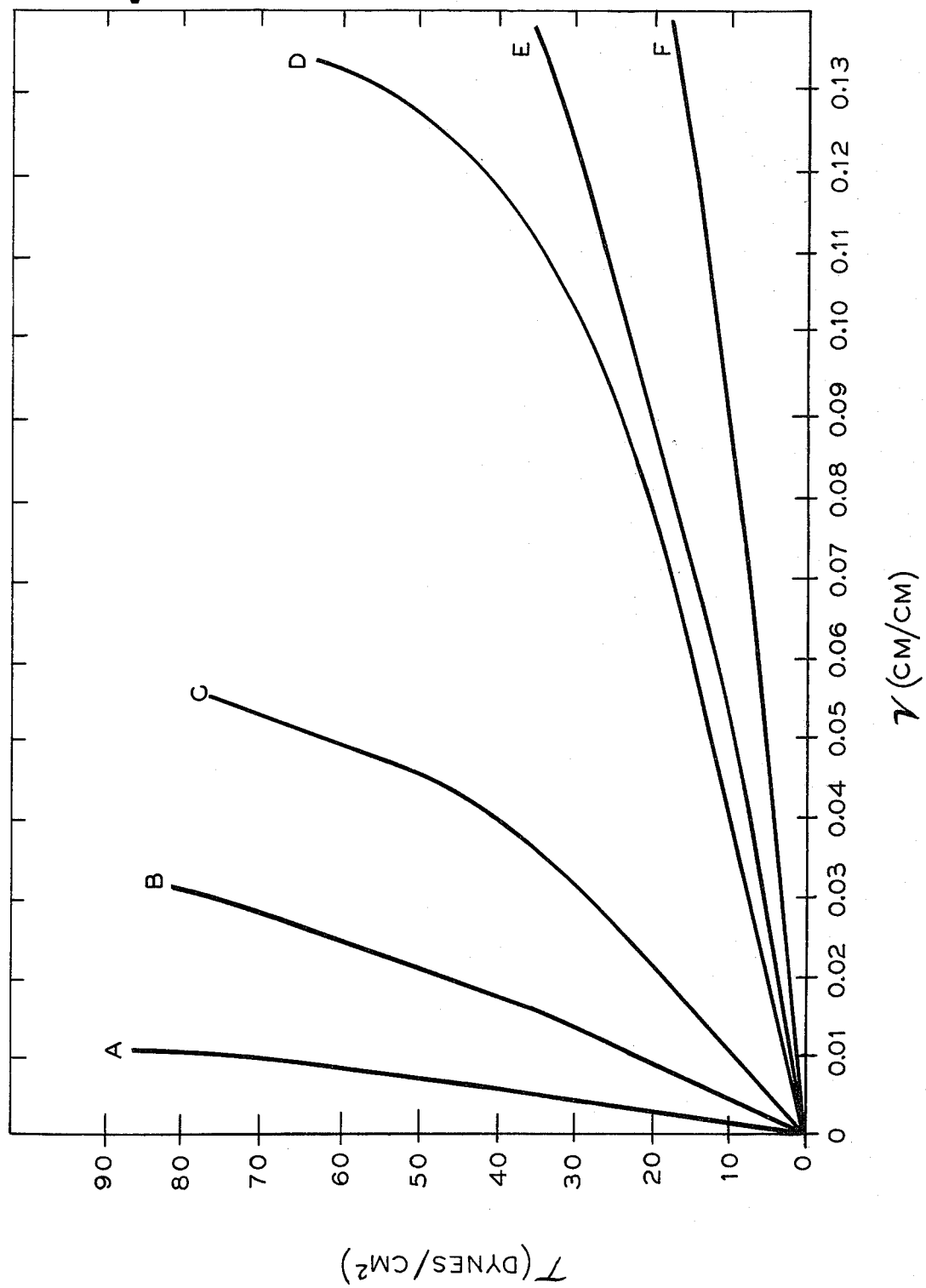
FIG. 9 is a chart illustrating the stress-strain curves of fibrin, plasma and blood clots.

The instrument 10 can be calibrated using the method described by Carr, Shen and Hermans (Analytical Biochemistry, 72, 202-211, 1976). Stress-strain curves in absolute units of some gels are illustrated in FIG. 9. The stress-strain curves were obtained using fibrin, plasma and blood clots and are identified as follows. A: 75% dog plasma clotted by recalcification, B: 2.5% mg/ml human fibrin clotted by 2 NIH units of thrombin per mg fibrinogen, C: 33% human blood clotted by recalcification (final Ca$^{++}$ concentration 6.67 mM), D: 33% human clotted by recalcification (final Ca$^{++}$ concentration 3.8 mM), E: 2 mg/ml bovine fibrin (65% clottable), 1 mM Ca$^{++}$, F: 0.6 mg/ml bovine fibrin (65% clottable), 1 mM Ca$^{++}$.

Before each measurement, the following adjustment procedures should be completed.

(1) Level the instrument frame 11.

(2) The disk 21 should be perfectly aligned to the center of the sample cup 19. This can be done by adjusting the knobs 46 and 47 on the micromanipulator 15. A constant 0.2 mm gap is preferred between the sample cup 19 and the tip of the disk 21. This may be done by using the fine adjustment control 48 on the micromanipulator 15.

In conducting a measurement, proper amounts of buffer and clotting materials such as fibrinogen solutions, plasma or blood are added to the sample cup 19. The mixture is incubated for approximately five minutes. Clotting is initiated by adding a proper amount of calcium chloride solution or thrombin solution, or both. The clotting mixture is thoroughly mixed, the sample disk 19 is then lowered into the clotting mixture with a slight tilting to avoid formation of bubbles. The transducer core 18 and magnetic coils 16 are then quickly pushed inward to a predetermined "in" position. Total time required up to this stage is about 20 seconds. The range selector of a transducer amplifier indicator (not shown) is placed at the least sensitive position. The movement of the meter needle indicates the relative position of the transducer core 18 in the LVDT body 36. The center or the zero position of the transducer core in LVDT 36 may be adjusted by turning the mounting plate 38 so that the indicator needle swings symmetrically to the middle point of the meter scale. A good practice in determing clotting t time is to permit the indicator needle to move continuously by applying a pulse of low DC current through the magnetic coils momentarily. The clotting time may be determined by the sudden increase in the damping of the needle movement. After the needle movement stops, the mounting plate 38 is again turned to gain an approximate zero position for the LVDT 36. The closer zero position may be obtained by a slight adjustment of the slide assembly 40. The indicator is then switched to an appropriate sensitivity range and the needle may be again zeroed with the zero adjustment on the indicator, if necessary. A current, usually 1 milliampere, is applied and the power supply is turned off immediately after recording the deflection of the transducer needle. The duration of application of the shear stress is usually between 2 to 5 seconds. Measurements are taken every 30 seconds to 10 minutes, depending on the progress of the clotting or lysis process. For stronger clots, larger current up to 100 milliamperes may be required to obtain a measurable displacement of the clot.

Using the instrument described, blood coagulation was studied in the following manner.

Bovine thrombin (Parke-Davis, Detroit) was dialyzed either in saline or in 0.1 M NaCl. Human blood or dog blood was drawn from healthy subjects and anticoagulated by adding 1 part of 3.8% sodium citrate to 9 parts of blood.

Platelet rich plasma (PRP) and platelet poor plasma (PPP) were prepared by centrifuging citrated blood at 280 g for 10 minutes and 4000 g for 20 minutes, respectively. Blood and PRP were kept in ice before using. PPP was stored in aliquotes at −75° C.

Figure 7:
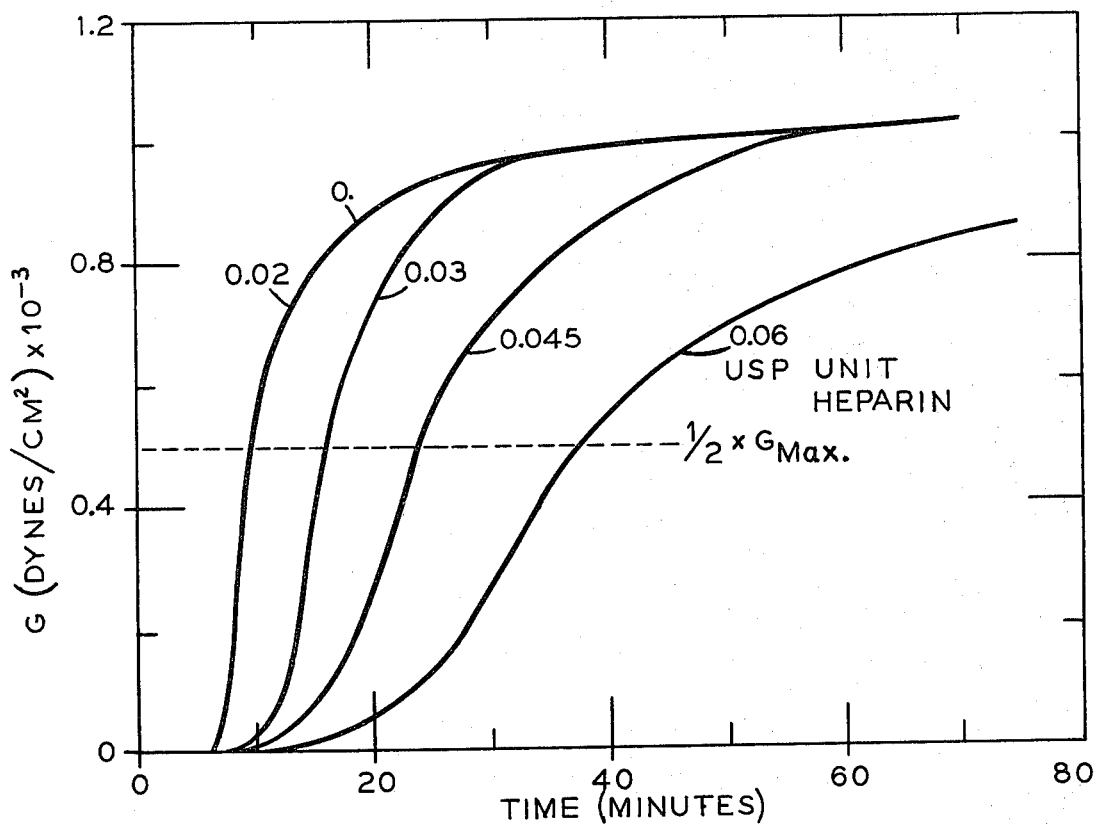
FIG. 7 is a chart illustrating kinetic traces of the clotting of human platelet poor plasma (ppp) upon recalcification with varying amounts of heparin.

FIGS. 7-10 illustrate the results obtained using the instrument of the present invention. FIG. 7 records the kinetic traces of the clotting of human ppp containing varying amounts of U.S.P. standard heparin. Gelation half-time, t (½), was determined as the time when elasticity of the clotting plasma reached half of the maximum rigidity (½×Gmax). t (½) may be used as a clotting parameter for determining heparin anticoagulant potency.

Figure 8:
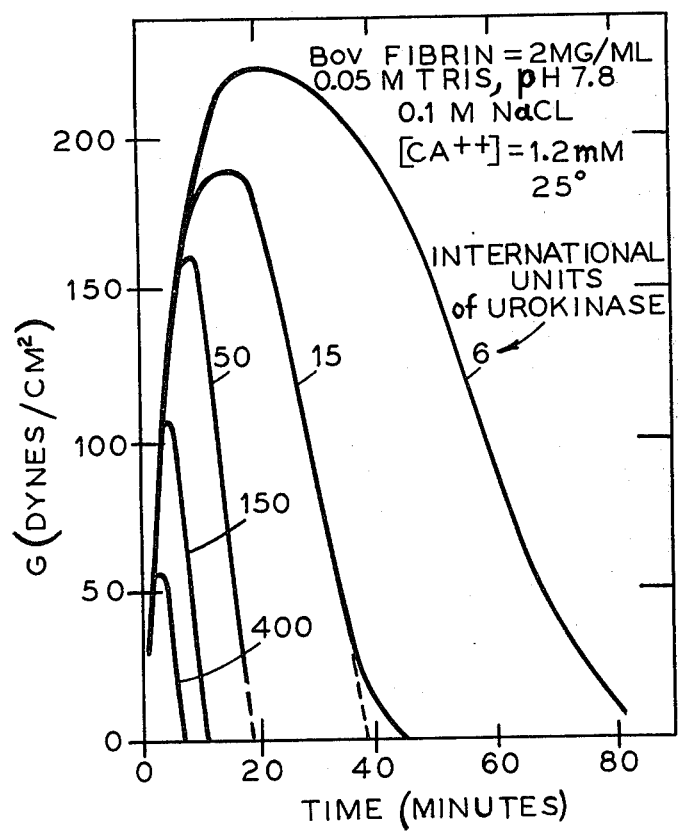
FIG. 8 is a chart illustrating kinetic traces of clotting and lysis processes of bovine fibrin with varying amounts of urokinase.

FIG. 8 records the kinetic traces of the clotting and lysis of bovine fibrin containing varying amounts of urokinase (in International Units) as described in the figure legend.

FIG. 9 illustrates the stress-strain curves of various fibrin, plasma and blood clots. Curve A is 75% dog plasma clotted by recalcification; curve B 2.5 mg/ml human fibrin clotted by 2 NIH units of thrombin per milligram of fibrinogen; curve C 33% human blood clotted by recalcification (6.67 mM $Ca^{++}$); curve D 33% human blood clotted by recalcification (3.8 mM $Ca^{++}$); curve E 2 mg/ml bovine fibrin (65% clottable), 1 mM $Ca^{++}$; and curve F 0.6 mg/ml bovine fibrin (65% clottable), 1 mM $Ca^{++}$.

Figure 10:
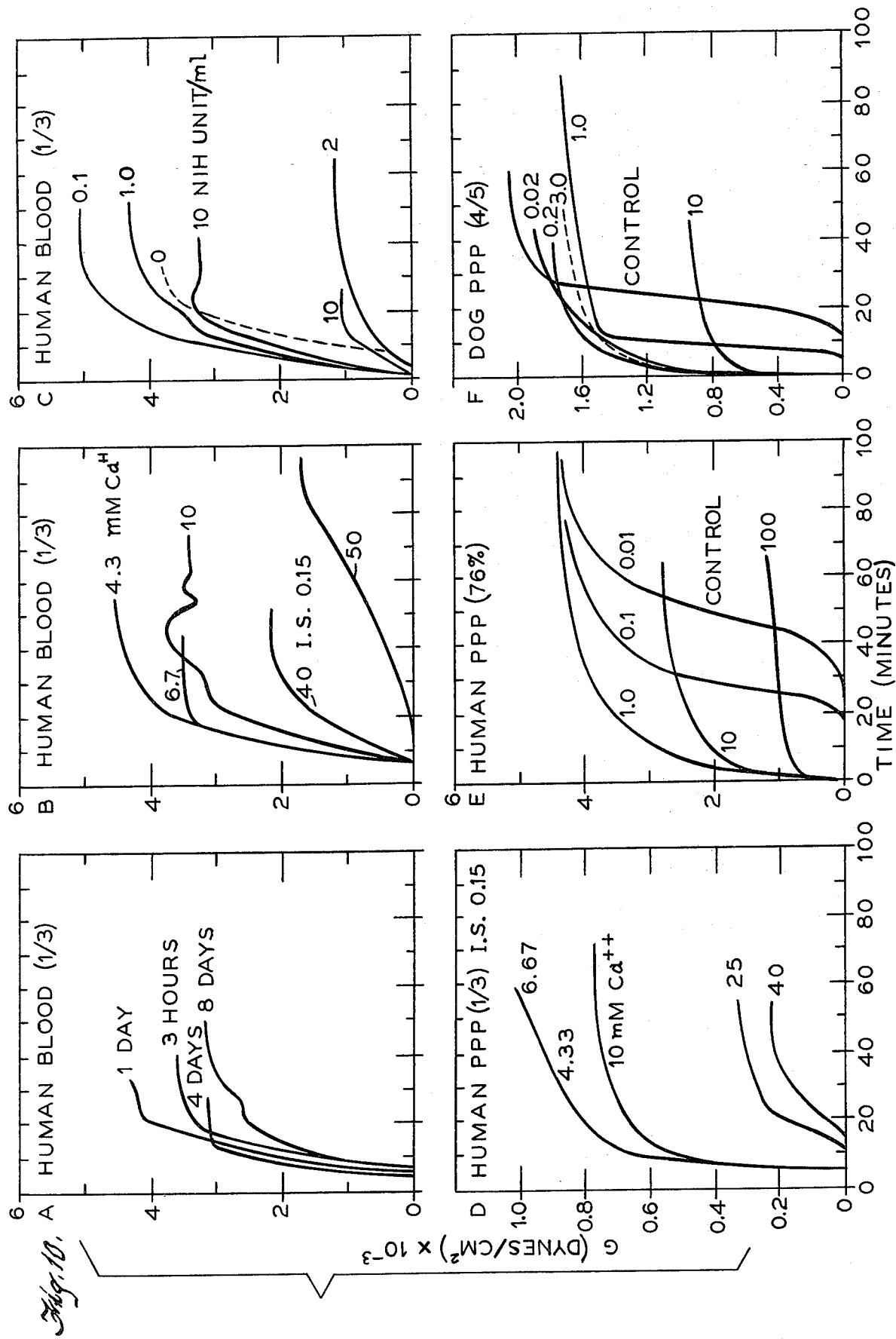
FIG. 10 is a series of charts illustrating the kinetics of the clotting of blood and plasma.

FIG. 10 illustrates the kinetics of the clotting of blood and plasma. FIG. 10-A illustrates the clotting of human blood (1 part blood, 2 parts buffer) as a function of storage time in ice, blood clotted by recalcification (6.67 mM $Ca^{++}$). FIG. 10-B illustrates the effect of calcium concentration (in mM) on the clotting of human blood. FIG. 10-C illustrates the effect of adding varying amounts of thrombin on the clotting of human blood with 6.67 mM $Ca^{++}$ (the 4 curves on the top) and without added calcium (the two curves on the bottom). FIG. 10-D illustrates the effect of calcium concentration on the clotting of human PPP, portions of saline were replaced by water to maintain ionic strength to a constant level of 0.15, no thrombin was used. FIG. 10-E illustrates the effect of adding varying amount of bovine thrombin on the clotting of human PPP by recalcification (20 mM $Ca^{++}$). FIG. 10-F illustrates the same as E except dog plasma (4 parts with 1 part saline) was used.

From FIG. 7 it is noted that each curve shows a linear portion near to the initial point. It is this initial slope which determines the rigidity modulus. Many factors determine the modulus: calcium ion concentration, dilution factor or fibrin concentration, fibrin species etc. FIG. 10-A shows the effect of storage time of human blood at 4° on the clotting process. For the first three days of storage, the clotting of whole blood shows small differences in clotting rate and in final rigidity (G max). Storage longer than three days slightly reduces G max, but the clotting rate still remains unchanged.

Effects of calcium concentration and ionic strength on the clotting of citrated human blood are demonstrated in FIG. 10-B. As expected, low level of calcium added to citrated blood causes slower clotting and forms weaker gels. There exists an optimum value of calcium concentration in favor of the clotting. Further increase in calcium concentration causes a decrease in both rate and final rigidity. This is not totally due to the increase in ionic strength which has been reported to have an effect causing decreases in clotting rate and final rigidity (Ferry and Morrison 1947, Shen and Hermans, 1975). This conclusion is supported by a curve in FIG. 10-B with $Ca^{++}$ concentration 40 mM and the ionic strength of the solution maintained at 0.15. Excess calcium ion obviously has certain unfavorable effect on clotting.

As indicated by FIG. 10-C, addition of small amounts of thrombin enhances clotting rates significantly. However, high thrombin concentration shows an adverse effect causing a reduction in final rigidity, probably due to contaminates in the thrombic preparation. A blood clot formed in the absence of calcium shows only about ⅓ of the maximum rigidity of the calcium clot. This is due to the reduction of both covalent crosslinking and the agglutination effect of calcium ions.

The clotting of human PPP upon recalcification was strongly affected by the amount of calcium added, in a similar manner to that observed in the clotting of whole blood. In FIG. 10-D, the ionic strength was kept constant in all the clotting curves. The optimal calcium concentration in favor of clotting and gelation is near 4–7 mM. The effect of higher calcium concentration in reducing rate and final rigidity is also clearly demonstrated in this illustration.

As shown in FIG. 10-E, the effect of thrombin on the clotting of PPP is even more obvious than that in the system of blood clotting.

What is claimed is:

1. An elastometer instrument for measuring the mechanical strength of gels comprising a frame member including a sample cup holder, a sample cup positioned in said holder, a sample disk and transducer core assembly suspended above the frame member, the disk being positionable into and out of the sample cup, electromagnetic means for applying a magnetic force to the transducer core assembly whereby torque is applied to the disk to thereby apply a shear stress to the sample in the sample cup when the disk is positioned in the sample, and a tranducer assembly for measuring the displacement of the sample when subject to the shear stress, said sample disk and transducer core assembly being suspended from a wire affixed to a micromanipulator adapted for precisely positioning the disk in the sample cup, and a precisely adjustable slide assembly adapted for positioning and control of the transducer assembly.

2. The elastometer instrument of claim 1 wherein the sample disk and transducer core assembly comprises a vertical connecting rod having the disk attached to the lower end thereof, a mounting chuck at the opposing end, and a transducer core arm secured substantially in the middle of the connecting rod in a position transverse thereto, and a magnet affixed to the connecting rod spaced from the sample disk.

3. The elastometer instrument of claim 2 wherein the electromagnetic means comprises opposed electromagnetic coils disposed about said magnet, in a spaced relationship.

4. The elastometer instrument of claim 3 wherein said sample disk and tranducer core assembly include a wire clamp disposed at each end of the wire, one of said clamps being adapted for attachment to the micromanipulator, the other being adapted for attachment to the mounting chuck on the connecting rod.

5. The elastometer instrument of claim 4 wherein the slide assembly for positioning and control of the transducer assembly comprises two superimposed assemblies, a lower slide assembly for providing coarse control and an upper slide assembly for providing fine adjustment.

6. The elastometer instrument of claim 5 wherein the electromagnetic coils are mounted on adjustable slide assemblies.

7. The elastometer instrument of claim 6 wherein the slide assembly for positioning and control of the transducer assembly and the slide assemblies having the electromagnetic coils mounted thereon are in turn mounted on a rotatable mounting plate.

8. The elastometer instrument of claim 7 wherein said sample cup holder includes channels therein for circulating fluid therethrough to thereby maintain the sample at a constant temperature.

* * * * *